United States Patent
Krsek

(10) Patent No.: US 6,638,533 B2
(45) Date of Patent: Oct. 28, 2003

(54) PULSE DOSAGE FORMULATIONS OF METHYLPHENIDATE AND METHOD TO PREPARE SAME

(76) Inventor: George Krsek, 5512 E. Burns St., Tucson, AZ (US) 85711

(*) Notice: Subject to any disclaimer, the term of this patent is extended or adjusted under 35 U.S.C. 154(b) by 18 days.

(21) Appl. No.: 10/038,571

(22) Filed: Jan. 3, 2002

(65) Prior Publication Data

US 2003/0129229 A1 Jul. 10, 2003

(51) Int. Cl.⁷ .............................................. A61K 9/24
(52) U.S. Cl. ....................... 424/472; 424/405; 424/470; 424/471
(58) Field of Search ................................ 424/472, 405, 424/471

(56) References Cited

U.S. PATENT DOCUMENTS

| | | | |
|---|---|---|---|
| 4,794,001 A | 12/1988 | Mehta et al. | 424/458 |
| 5,733,756 A | 3/1998 | Zeitlin et al. | 435/122 |
| 5,837,284 A | 11/1998 | Mehta et al. | 424/459 |
| 5,874,090 A | 2/1999 | Baker et al. | 424/400 |
| 5,908,850 A | 6/1999 | Zeitlin et al. | 514/315 |
| 5,922,736 A * | 7/1999 | Dariani et al. | 514/317 |
| 5,936,091 A | 8/1999 | Khetani et al. | 546/233 |
| 5,965,734 A | 10/1999 | Ramaswamy et al. | 546/233 |
| 6,025,502 A | 2/2000 | Winklter et al. | 549/21 |
| 6,100,401 A | 8/2000 | Prashad et al. | 546/238 |
| 6,162,919 A | 12/2000 | Prashad et al. | 546/233 |
| 6,217,904 B1 | 4/2001 | Midha et al. | 424/468 |
| 6,242,464 B1 | 6/2001 | Harris et al. | 514/317 |
| 6,255,325 B1 | 7/2001 | Dariani et al. | 514/317 |
| 6,555,136 B2 | 4/2003 | Midha | 424/469 |

OTHER PUBLICATIONS

Srinivas, et al., "Enantioselective Pharmacokinetics and Pharmacodynamics of dl–threo–methylphenidate in Children with Attention Deficit Hyperactivity Disorder", 1992, pp. 561–568.

Patrick, et al., "Pharmacology of the Enantiomers of threo–Methylphenidate", 1987, pp. 152–158; Patrick, et al., The Absorption of Sustained–Release Methylphenidate Formulations Compared to an Immediate–Release Formulation, 1989, pp. 165–171.

Ding, et al., "Chiral Drugs: Comparison of the Pharmacokinetics of [$^{11}$C]d–threo and l–threo–methylphenidate in the Human and Baboon Brain", 1997, pp. 131:71–78.

Srinivas, et al., "Stereoselective Disposition of Methylphenidate in Children with Attention–Deficit Disorder", 1987, pp. 300–306.

Hubbard, et al., Enantioselective Aspects of the Disposition of all–threo–Methylphenidate after the Administration of a Sustained–Release Formulation to Children . . . , 1989, pp. 944–947.

* cited by examiner

Primary Examiner—Thurman K. Page
Assistant Examiner—Micah-Paul Young
(74) Attorney, Agent, or Firm—Dale F. Regelman

(57) ABSTRACT

Dosage forms comprising pulse release formulations for oral administration of a Methylphenidate drug are provided. The dosage forms provide a substantially immediate dose of methylphenidate upon ingestion, followed by one or more additional doses at predetermined times. By providing such a drug release profile, the dosage forms eliminate the need for a patient to carry an additional dose for ingestion during the day. The dosage forms and methods provided are useful in administering Methylphenidate and pharmaceutically acceptable salts thereof, which generally require one or more doses throughout the day.

25 Claims, 6 Drawing Sheets

PULSE DOSAGE FORMULATIONS OF METHYLPHENIDATE AND METHOD TO PREPARE SAME

FIELD OF THE INVENTION

Applicant's invention relates to improved dosing of medications. In particular, the present invention relates to improved dosing of a medication whereby two or more effective pulse dosages may be provided by administration of a pulse release formulation. Effective administration of the second pulse dosage is time-delayed following oral ingestion of Applicant's pulse release formulation.

Applicant's dosage forms and methods are particularly suitable for the administration of methylphenidate hydrochloride, and especially for the administration of a single isomer, d-threo-methylphenidate hydrochloride ("DTMP"). Applicant's method of administration of a pulse release formulation which contains a first pulse release dosage in combination with a second pulse release dosage provides for reduced abuse potential, improved convenience of administration, and better patient compliance, especially when methylphenidate is used to treat certain central nervous system disorders.

BACKGROUND OF THE INVENTION

Attention Deficit Disorder (ADD), a commonly diagnosed nervous system illness in children, is often treated with methylphenidate hydrochloride. Methylphenidate is sold in commerce under the name Ritalin®. Ritalin is a registered trademark owned by Novartis Corporation.

Symptoms of ADD include distractibility and impulsivity. A related disorder, termed Attention Deficit Hyperactivity Disorder (ADHD), is further characterized by symptoms of hyperactivity, and is also treated with methylphenidate hydrochloride. Methylphenidate drugs have also been used to treat cognitive decline in patients with Acquired Immunodeficiency Syndrome (AIDS) or AIDS related conditions. See, e.g., Brown, G., Intl. J. Psych. Med. 25(1): 21–37 (1995); Holmes et al., J. Clin. Psychiatry 50:5–8 (1989). Other embodiments of the present invention provide symptomatic treatment for narcolepsy, depression, as well as for mood elevation, particularly, in terminally ill patients with diseases such as cancer. These various treatment regimes comprise administering to the patient one of Applicant's pulse release formulations providing once-daily oral administration of a methylphenidate drug such as methylphenidate hydrochloride.

Methylphenidate exists as four separate optical isomers. These four optical isomers are shown below.

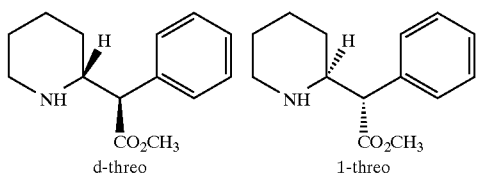
d-threo                 l-threo

-continued

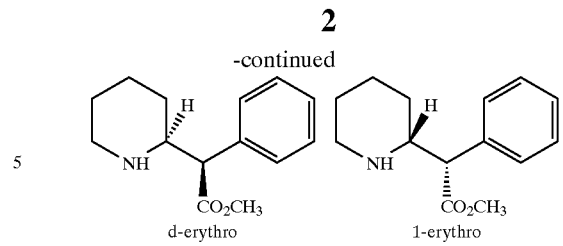
d-erythro               l-erythro

Pharmaceutically acceptable salts of Methylphenidate, the hydrochloride for example, are sometimes administered clinically. Other phenidate drugs can also can be administered according to Applicant's invention.

Clinically, the threo pair of enantiomers of methylphenidate hydrochloride is generally administered for the treatment of ADD and ADHD. The hydrochloride salt is commonly referred to simply as "methylphenidate". Unless indicated otherwise, the term "Methylphenidate" is used broadly herein to include methylphenidate and pharmaceutically acceptable salts thereof, including methylphenidate hydrochloride.

The threo racemate (pair of enantiomers) of Methylphenidate is a mild central nervous system stimulant with pharmacological activity qualitatively similar to that of amphetamines. Undesirable side effects associated with the use of the dl-threo racemate of Methylphenidate include anorexia, weight loss, insomnia, dizziness and dysphoria. Furthermore, the racemate, which is a Schedule II controlled substance, produces a euphoric effect when administered intravenously or through inhalation or ingestion, and thus carries a high potential for abuse.

It is known in the art that the pharmacodynamic activity of dl-threo-methylphenidate resides in the d-threo isomer (Clin. Pharmacol. Ther., 52:561–568 (1992)). Therefore, while dl-threo-methylphenidate is generally used therapeutically, this racemate includes the l isomer which apparently makes no significant contribution to the pharmacological effectiveness of the drug, but likely contributes to the associated side effects. It is thus desirable to administer only the active d-threo form of the drug.

Children being treated with dl-threo methylphenidate must generally take one or more doses during the day. This creates a problem for school administrators who must store a controlled substance on school premises, with the associated risk that it may be stolen for illicit use. Furthermore, children may be traumatized by ridicule from peers when they must take medication at school.

A need exists for a pulse release formation, and method to prepare same, that delivers Methylphenidate with maximum effectiveness, and with minimal potential for abuse. Furthermore, a need exists for a dosage form which provides, in one administration, an initial release followed, at a predictable delay, by a second release, of maximally effective methylphenidate. This will eliminate the risk of theft or loss of the second dose, while minimizing undesirable side effects and maximizing ease of administration. Applicant's invention is directed to these, as well as other, important ends.

SUMMARY OF THE INVENTION

Applicant's invention includes a dosage form for the oral administration of Methylphenidate, where that dosage form includes a first pulse dosage and a second pulse dosage. Applicant's first pulse dosage includes a Methylphenidate portion and a sealing layer disposed over that Methylphenidate portion. Applicant's second pulse dosage includes a Methylphenidate portion, a first sealing layer disposed over that Methylphenidate portion, a polymeric coating layer disposed over the first sealing layer, and a second sealing layer disposed over the polymeric coating layer.

Applicant's invention further includes a method to prepare Applicant's first pulse dosage, Applicant's second pulse dosage, and Applicant's pulse release formulations. Applicant's invention further includes methods to treat ADD, ADHD, AIDs-related conditions, narcolepsy, acute depression, and for elevating the mood of terminally ill patients.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
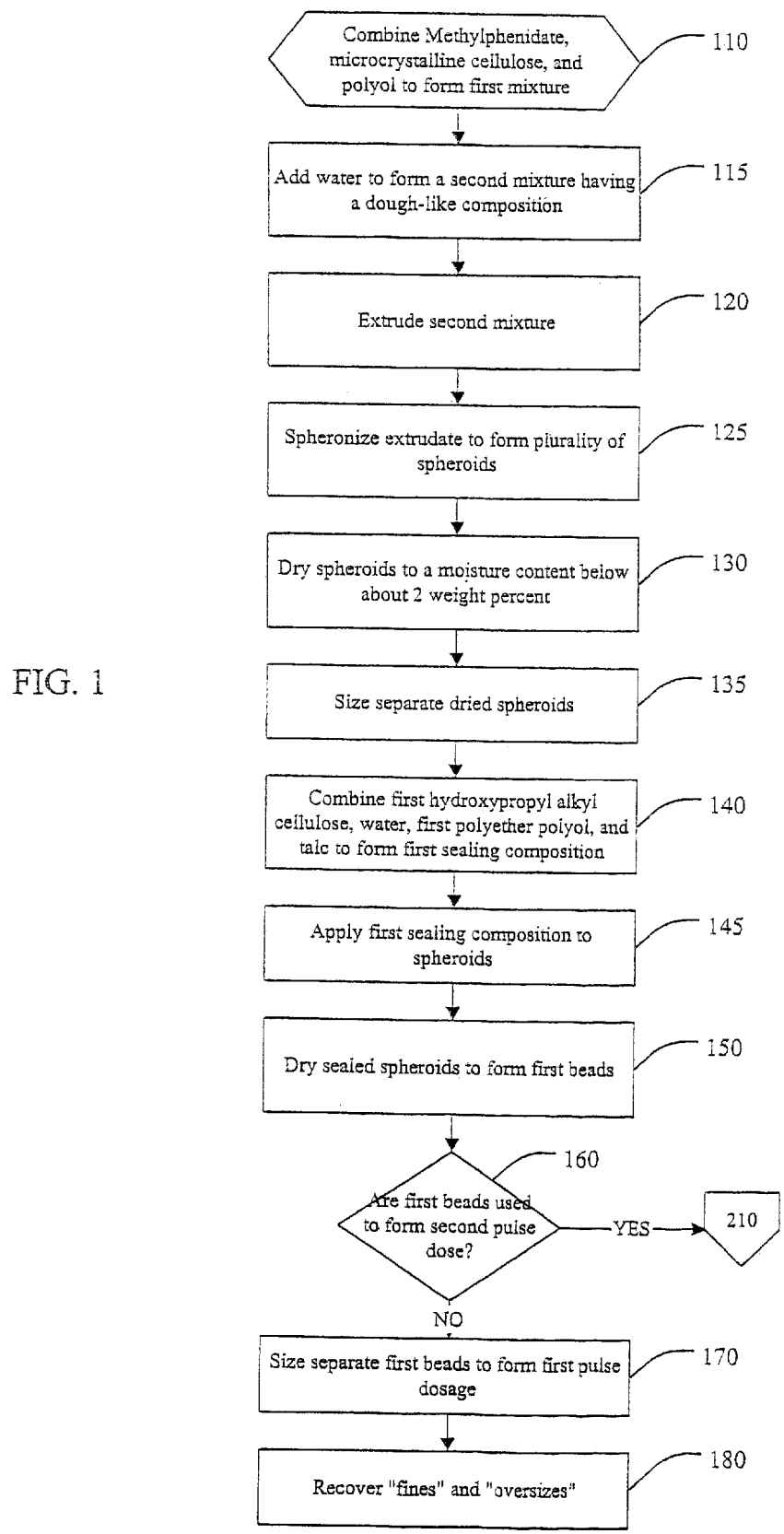
FIG. 1 is a flow chart summarizing the steps of Applicant's method to prepare Applicant's first pulse dosage.

The invention will be described as embodied in pulse release dosages, and pulse release formulation which includes those pulse release dosages, to deliver two or more doses of Methylphenidate. The following description of Applicant's composition and method is not meant, however, to limit Applicant's invention to the delivery of the d-threo isomer of methylphenidate only, as Applicant's invention herein can be applied to the pulsed delivery of phenidate drugs in general, including the four isomers of Methylphenidate and the four isomers of Methylphenidate hydrochloride. References made herein to "Methylphenidate," includes all four optical isomers of the compound and all pharmaceutically acceptable salts thereof. When one or more particular isomers is contemplated, the isomer is indicated, as in d-threo, l-threo, etc. The combined threo isomers may be indicated simply as "threo" and the combined erythro isomers as "erythro". For therapeutic use in treating conditions treatable by methylphenidate drugs, dl-threo methylphenidate hydrochloride is generally used, while d-threo methylphenidate hydrochloride is preferred according to the present invention.

As discussed, the four isomers have exhibited varying levels of therapeutic activity, and have been shown to differ generally in producing unwanted side effects. The present invention provides dosage forms which maximize therapeutic effectiveness and minimize undesirable side effects. In certain preferred embodiments, the dosage forms of the present invention provide administration of the two threo forms of methylphenidate. In particularly preferred embodiments, the dosage forms of the present invention provide administration of a single isomer, d-threo-methylphenidate, albeit in two or more doses.

The present invention provides, in one embodiment, a therapeutic composition for the oral administration of Methylphenidate comprising a pulse release formulation containing two groups of particles, each containing Methylphenidate. The term "particles", as used herein, includes pellets, granules, and the like.

The first group of particles, i.e. Applicant's first pulse dosage, provides a substantially immediate dose of Methylphenidate upon ingestion by a mammal. In certain embodiments, Applicant's first pulse dosage also comprises a sealant. The second group of particles, i.e. Applicant's second pulse dosage, comprises Methylphenidate-containing particles encapsulated with a first sealant, a polymeric coating, and a second sealant. In certain embodiments, the first sealant is the same as the second sealant. In certain embodiments, the first sealant differs from the second sealant.

The combination of the first sealant, the polymeric coating, and the second sealant, comprises a pharmaceutically acceptable encapsulant in an amount sufficient to provide a delay of from about 2 hours to about 7 hours following ingestion before release of the second dose of Methylphenidate. If desired, one or more additional doses may be delivered by additional particles, coated in a similar manner, but with a sufficient amount of Applicant's first sealant, polymeric coating, and second sealant to provide the dosage after an additional delay. Methylphenidate and pharmaceutically acceptable salts thereof, including methylphenidate hydrochloride, can be prepared into the dosage forms of the invention.

The amount of Methylphenidate in each group of particles can vary, depending upon the dosage requirements of the patient to whom the drug is to be administered. Generally, the daily dosage requirement for methylphenidate drugs is from about 1 mg to about 50 mg per day, preferably from about 2 mg to about 20 mg, and more preferably from about 2.5 to about 12 mg per day. The actual dosage to be administered will be determined by the attending physician as a matter of routine.

In certain embodiments, Applicant's first pulse dosage comprises up to about 99 weight percent Methylphenidate powder. In other embodiments of Applicant's first pulse dosage, depending upon the amount of sealant, microcrystalline cellulose, and polyol, the Methylphenidate is present in an amount from about 22 weight percent to about 65 weight percent of Applicant's first pulse dosage. Depending on the amount of first sealant, polymeric coating, and second sealant, Methylphenidate is present in Applicant's second pulse dosage in an amount between about 20 weight percent and about 60 weight percent.

The pulse release formulations of the present invention are intended for oral ingestion by a mammal, particularly a human. The dosage forms of the present invention are particularly suitable for the administration of methylphenidate drugs, in at least two doses. Most preferably, the dosage forms provide two doses of a d-threo methylphenidate drug such as d-threo methylphenidate hydrochloride. The second dose can be delayed by from about 2 hours to about 7 hours, preferably from about 3 hours to about 6 hours, and most preferably from about 4 hours to about 5 hours, following ingestion of the dosage form by a mammal. This eliminates the need for a patient, for example a child being treated for ADD, to carry a second dose for ingestion __several hours after ingestion of a first dose. The exclusion of the l isomers and the d-erythro isomer eliminates the concurrent ingestion of forms of methylphenidate principally believed to be associated with adverse side effects and/or reduced effectiveness.

The temporal separation of the two or more doses of Methylphenidate provided according to the present invention can be referred to as "pulsatile". The release of the first dose of Methylphenidate from Applicant's first pulse dosage preferably occurs substantially immediately; for example, within about 30 minutes following administration. Following a period of little or substantially no drug release, the second dose of Methylphenidate is released from Applicant's second pulse dosage. Thus, the two releases can be referred to as "pulses."

"Immediate release", as used herein, means release within about a half hour following ingestion, preferably about 15 minutes, and more preferably within about 5 minutes following ingestion. "Delayed release", as used herein, refers to a drug release profile which includes a period during which no more than about 10 percent of the drug in a particular dosage form is released, followed by a period of from about 0.5 hour to about 2.5 hours, preferably about 1.5 hours, more preferably about 1 hour, in which no less than about 70 percent, preferably no less than about 80 percent, and more preferably no less than about 90 percent, of the drug is released. The terms "medication" and "drug" are used interchangeably herein.

According to the present invention, delayed release dosage forms can be combined with forms which provide immediate release of a drug. Thus, two or more dosage forms can be combined, one dosage form providing a portion of a patient's daily dosage needs of a drug and subsequent dosage forms providing additional portions of a patient's daily dosage needs. For example, a drug can be administered to a patient in two dosage forms simultaneously, one providing, e.g., about 30–50 percent of the patient's daily requirement of the drug and the second providing the remainder of the patient's daily requirement. Alternatively, and preferably, a single dosage form can be administered which includes an immediate dose of some portion of a patient's daily requirement and one or more delayed doses to provide the remaining portion or portions of the patient's daily requirement.

Dosage forms of the present invention provide an initial dose of a drug such as, for example, a pharmaceutically acceptable salt of d-threo-methylphenidate, followed by an interval wherein substantially no additional drug is released, followed in turn by release of a second dose. If desired, a second substantially release-free interval may be provided following the second release, followed in turn by a third dose. Thus, dosage forms providing 3 or more doses are contemplated by the present invention. However, dosage forms providing 2 or 3 doses are generally preferred for therapeutic use, with 2 doses being more preferred. For example, the first dose can provide from about 30 percent to about 70 percent of a patient's daily prescribed intake of the drug and the second dose provides from about 70 percent to about 30 percent. If two approximately equal doses are desired, the initial dose preferably provides from about 40 percent to about 60 percent, and the second dose preferably provides from about 60 percent to about 40 percent, of a patient's prescribed daily intake of the drug. If desired, the first dose and the second dose can each provide about 50 percent of a patient's prescribed daily intake of drug. However, as will be apparent to one skilled in the art, the effect of drug metabolism in the body may require adjustment of the relative amounts of each dose, so that, for example, the second dose may have to be adjusted to provide more of the drug than the first dose, to compensate for any competition between drug release and drug metabolism.

The initial dose of Methylphenidate in the dosage forms of the present invention can be provided by incorporating Methylphenidate into a form which allows for substantially immediate release of the drug once the dosage form is ingested by a patient. Such forms include, for example, spheroidal, Methylphenidate-containing particles covered with a sealant. The dose for immediate release can be administered in a tablet or capsule form which may also include the delayed dose. For example, two or more groups of Methylphenidate-containing spheroids may be combined within a hard gelatin capsule or compressed into a tablet.

Dosage forms of the present invention preferably comprise particles containing d-threo methylphenidate. In one embodiment, the dosage form comprises two groups of particles. A first group of particles, i.e. Applicant's first pulse dosage, provides the initial dose of d-threo methylphenidate. The second group of particles, i.e. Applicant's second pulse dosage, provides a delayed dose of d-threo methylphenidate.

FIG. 1 summarizes the steps in Applicant's method to form Applicant's first pulse dosage. In step 110, Methylphenidate is combined with microcrystalline cellulose particles and a polyol to form a first mixture. In certain embodiments, these ingredients are dry blended for at least about 15 minutes. In certain embodiments, the Methylphenidate is present in Applicant's first mixture at a level between about 25 weight percent and about 75 weight percent. In certain embodiments, Methylphenidate is present in the first mixture at a level of about 40 weight percent. In certain embodiments, Methylphenidate is present in the first mixture at a level of about 57 weight percent. In certain embodiments, Methylphenidate is present in the first mixture at a level of about 66 weight percent.

In certain embodiments, the microcrystalline cellulose particles have a typical particle size of about 50 microns and about 200 microns. In certain embodiments, the microcrystalline cellulose particles have a bulk density of between about 0.25 g/cc and about 0.45 g/cc. In certain embodiments, the microcrystalline cellulose particles have a typical particle size of about 50 microns and a bulk density of about 0.29 g/cc.

As those skilled in the art will appreciate, many polyols are hygroscopic. Applicant has found, however, that the polyol used in step 110 must be substantially moisture free. In certain embodiments, the polyol used in step 110 is first dried to a moisture level of about one weight percent or less. Applicant has found that use of certain polyols having a greater moisture level results in less than optimal mixing of the methylphenidate and the microcrystalline cellulose.

In certain embodiments, the polyol of step 110 comprises a carbohydrate. In certain of these embodiment, the carbohydrate used in step 110 comprises a spray-dried sugar. In certain embodiments, the polyol of step 110 comprises spray-dried lactose.

In step 115, water is added to the stirred first mixture to form a second mixture. In certain embodiments, the water is added over a period of between about 5 to about 30 minutes. Applicant has found that the water component must be added over at least a 5 minute time period in order to form a second mixture having the requisite dough-like consistency. In certain embodiments, the second mixture has a bulk viscosity of greater than about 10,000 cps. In certain embodiments, the second mixture has a bulk viscosity of greater than about 50,000 cps.

In certain embodiments, the second mixture has a bulk viscosity of greater than about 100,000 cps.

In step 120, the second mixture is extruded. In certain embodiments, step 120 includes using a basket-extruder. In certain embodiments, this extruder includes openings of about 3/64 inch in diameter. Applicant has found that openings of this size produce cylindrically-shaped extrudates having an optimal diameter for further processing. In certain embodiments, the extrudate comprises a plurality of cylindrical particles having an average diameter of about 0.05 inch and an average length of about 2 inches. In certain embodiments, the extrudate comprises cylindrical materials having an average diameter of about 0.05 inch and an average length of about 1 inch. In certain embodiments, the extrudate comprises cylindrical materials having an average diameter of about 0.05 inch and an average length of about 0.5 inches.

Applicant has further discovered that the extrudate of step 120 should be dry to the touch. If the extrudate of step 120 contains too much water, then that extrudate tends to agglomerize. If the extrudate of step 120 contains too little water, then an excess amount of "fines" are formed in the spheronization of step 125. In certain embodiments, the extrudate of step 120 has a moisture level between about 10 weight percent and about 30 weight percent. In certain embodiments, the extrudate of step 120 has a moisture level of about 25 weight percent.

In step 125 the cylindrical extrudate of step 120 is spheronized to form spheroids. The diameter of the spheroids formed in step 125 is determined by the diameter of the extrudate formed in step 120. The spheres formed in step 125 have diameters which average between about 0.01 inch to about 0.1 inch. In certain embodiments, the spheres formed in step 125 have an average diameter of about 0.05 inch.

In certain embodiments, step 125 includes use of an apparatus comprising a drum having a rotating textured disc at its base is used to form the spheroidal-shaped particles from the cylindrical extrudate. In certain embodiments, step 125 includes operating the spheronizer at a speed of between about 500 rpm and about 1800 rpm. In certain embodiments, step 125 includes forming spheroids from the extrudate of step 120 using a spheronizer operated at a speed of about 1,000 rpm. In certain embodiments, Applicant's method includes operating the spheronizer for a time period between about 5 seconds and about 20 seconds. In certain embodiments, step 125 includes operating the spheronizer for about 10 seconds.

In step 130, the particles formed in step 125 are dried. In certain embodiments, the Methylphenidate-containing particles are placed in a tray and are dried in an air oven operated at about 45° C. In certain embodiments, the Methylphenidate-containing particles are dried in step 130 to a moisture level of between about 1 weight percent and about 4 weight percent. In certain embodiments, the Methylphenidate-containing particles are dried to a moisture level of below about 2 weight percent.

In step 135, the dried, Methylphenidate-containing spheroids formed in step 130 are separated according to size. In certain embodiments, the dried spheroids of step 130 are first separated using a 12 mesh screen. Those particles that do not pass through such a 12 mesh screen comprise "oversizes." The spheroids that pass through the 12 mesh screen are then further separated using a 25 mesh screen. The spheroids that pass through such a 25 mesh screen comprise "fines." The spheroids that pass through the 12 mesh screen and that do not pass through the 25 mesh screen are coated with a sealant in step 145.

As those skilled in the art will appreciate, Methylphenidate comprises a controlled substance. Therefore, the starting quantities of Methylphenidate used in step 110 must be accounted for. The oversizes and fines separated in step 135 are recovered and weighed. The weights of these oversizes and fines are used to account for the starting quantities of Methylphenidate. Because Applicant's method to form pulse release dosages includes extruding/spheronizing methylphenidate-containing particles rather than spraying Methylphenidate onto a carrier, such as non-pareil beads, accounting for the starting quantities of Methylphenidate is considerably easier using Applicant's method than using prior art methods.

In step 140, Applicant's first sealing composition is prepared. A sealant provides a physical barrier between the drug and either a coating or the environment. Suitable sealants can be prepared from materials such as biologically inert, permeable, pharmaceutically acceptable materials, such as, for example, hydroxypropylalkylcelluloses, wherein "alkyl" refers to C1–C6 hydrocarbon chains. Exemplary materials include hydroxypropylmethylcellulose, hydroxypropylethylcellulose, hydroxypropylpropylcellulose, and hydroxypropylbutylcellulose. Hydroxypropylmethylcellulose is preferred.

In step 140, a first hydroxypropylalkylcellulose, a first polyether polyol, and talc are combined to form Applicant's first sealant material. Applicant's first sealing composition comprises Applicant's first sealant material in combination with water. In certain embodiments, Applicant's first sealing material is present in Applicant's first sealing composition at a level between about 25 weight/volume percent and about 55 weight 1 volume percent. In certain embodiments, Applicant's first sealing material is present in Applicant's first sealing composition at a level between about 30 weight/volume percent and about 50 weight/volume percent. In certain embodiments, Applicant's first sealing material is present in Applicant's first sealing composition at a level of about 45 weight/volume percent, i.e. about 45 grams of sealing material in about 100 ml of water.

In certain embodiments, the talc used in step 140 comprises Magnesium Silicate Hydroxide, i.e. $Mg_3Si_4O_{10}(OH)_2$.

In certain embodiments, the talc used in step 140 comprises Magnesium metasilicate, i.e. $MgSiO_3$. In certain embodiments, the talc used in step 140 comprises Magnesium, orthosilicate, i.e. $Mg_2SiO_4$.

In certain embodiments, the first polyether polyol used in step 140 comprises a polyethyleneoxide diol. In certain embodiments, the first polyether polyol used in step 140 comprises a polyethyleneoxide triol. In certain embodiments, the first polyol used in step 140 comprises a polypropyleneoxide diol. In certain embodiments, the first polyol used in step 140 comprises a polypropyleneoxide triol. In certain embodiments, the first polyol used in step 140 comprises a tetramethyleneoxide diol. In certain embodiments, the first polyol used in step 140 comprises a tetramethyleneoxide triol.

In certain embodiments, the first polyether polyol used in step 140 has a hydroxyl equivalent weight of between about 100 and about 800. In certain embodiments, the first polyether polyol used in step 140 has a hydroxyl equivalent weight of between about 200 and about 600. In certain embodiments, the first polyether polyol used in step 140 has a number average molecular weight of between about 200 and about 800.

In step 145 the spheroids of step 135 are covered with the first sealing composition of step 140. In certain embodiments, Applicant's spheroids of step 135 are sprayed with Applicant's sealing composition. In certain embodiments, Applicant's spheroids of step 135 are added to a fluidized bed having a bottom spray configuration. In certain embodiments, the fluidization airflow was between about 70 and about 80 m³/hour. In certain embodiments, the atomization air pressure used as 1.5 bar. In certain embodiments, the fluidized bed was maintained at a temperature of about 50° C. In certain embodiments, Applicant's sealing IF composition was sprayed at a rate from about 2 g/minute to about 5 g/minute.

In step 150, the Methylphenidate-containing particles covered with Applicant's first sealing composition are sealed to form Applicant's first beads. In certain embodiments, step 150 includes drying the sealing composition-covered spheres in the fluidized bed apparatus for about 5 minutes at a temperature of about 55° C. In certain embodiments, step 150 includes drying the sealing composition-covered spheres in an air oven for 24 about 24 hours at 55° C.

In step 160, it is determined whether the first beads of step 150 will be used to form Applicant's second pulse dosage. In the event Applicant's first beads are used to form Applicant's second pulse dosage, then Applicant's method transitions to step 210.

On the other hand, if the first beads of step 150 are used to form Applicant's first pulse dosage, then Applicant's method transition to step 170. In step 170, the first beads are separated by size. In certain embodiments, step 170 includes separating the first beads of step 150 using a 12 mesh screen. In certain embodiments, step 170 includes separating the first beads of step 150 that pass through a 12 mesh screen using a 25 mesh screen. In certain embodiments, the first beads of step 150 that pass through a 12 mesh screen, but not pass through a 25 mesh screen, comprise Applicant's first pulse dosage. In step 180, the fines and oversizes separated in step 170 are collected and weighed.

Figure 3:
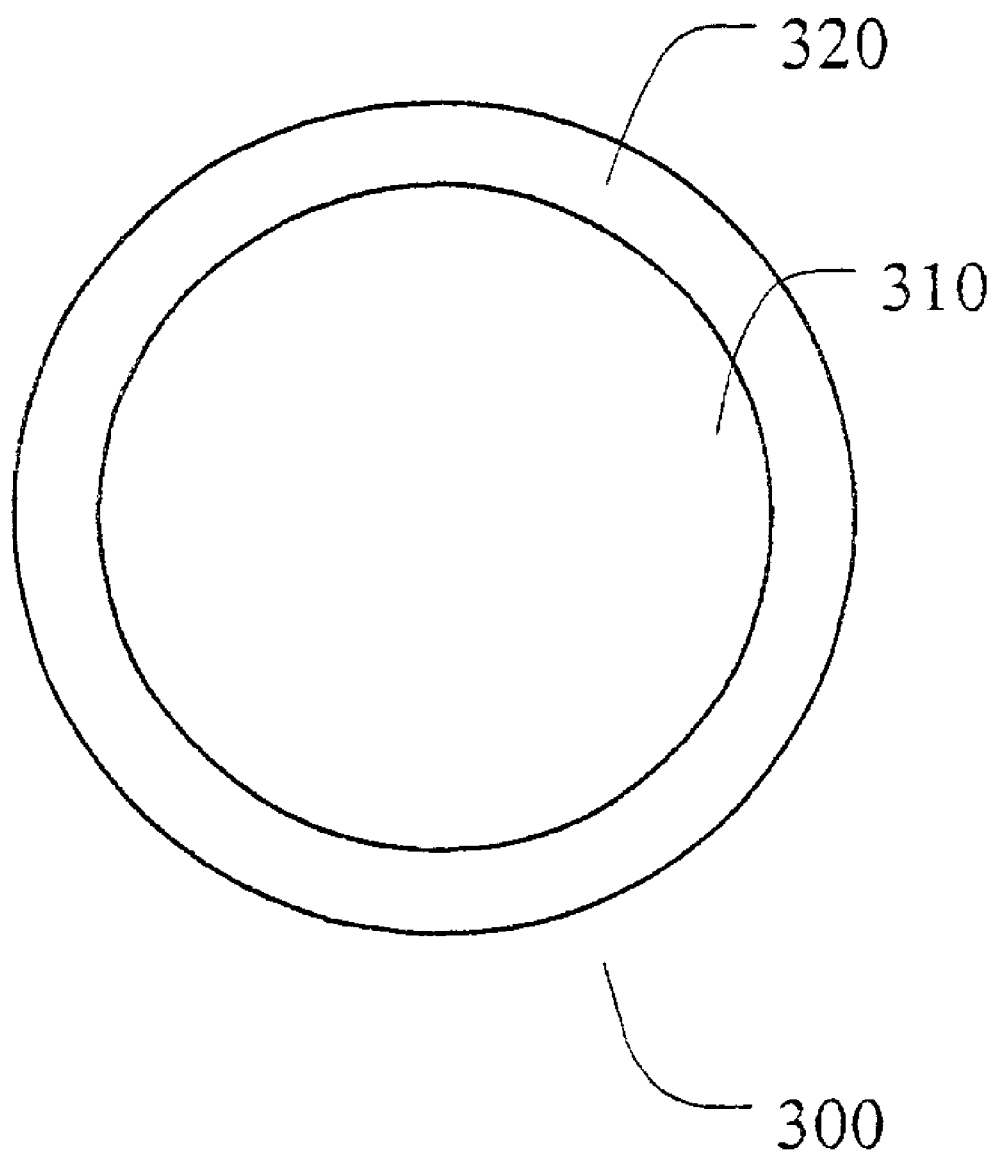
FIG. 3 is a cross sectional view of one embodiment of Applicant's first pulse dosage.

Referring to FIG. 3, Applicant's first pulse dosage 300 includes Methylphenidate-containing portion 310 covered by sealing layer 320. In certain embodiments, Methylphenidate-containing portion 310 comprises the spheroidal-shaped particles separated in step 135. In certain embodiments, Methylphenidate-containing portion 310 is present in first pulse dosage 300 at a level between about 45 weight percent and about 65 weight percent. In certain embodiments, Methylphenidate-containing portion 310 is present in first pulse dosage 300 at a level between about 50 weight percent and about 60 weight percent. In certain embodiments; Methylphenidate-containing portion 310 is present in first pulse dosage 300 at a level of about 55 weight percent.

Figure 2:
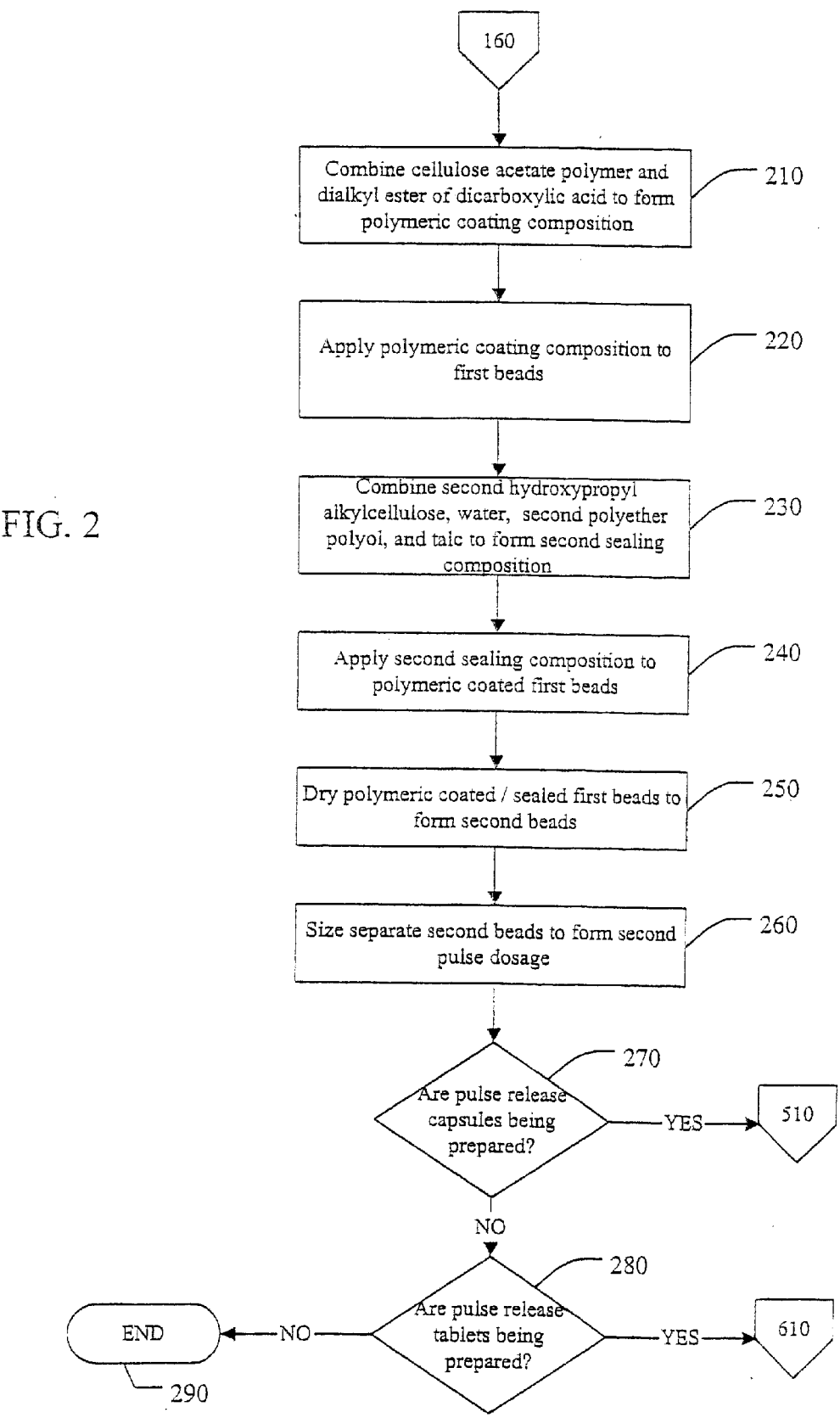
FIG. 2 is a flow chart summarizing the steps of Applicant's method to prepare Applicant's second pulse dosage.

Referring now to FIG. 2, in step 210 a polymeric coating composition is formed using a cellulose acetate polymer in combination with a dialkyester of a dicarboxylic acid, where that dicarboxylic acid contains at least six carbon atoms. In certain embodiments, Applicant's coating composition comprises a cellulose acetate phthalate polymer. In certain embodiments, Applicant's coating composition includes an aqueous dispersion comprising about 30 percent by weight of a cellulose acetate phthalate polymer. In certain embodiments, Applicant's coating composition includes a liquid (at room temperature) dialkyl ester of decanedioic acid, having the formula:

$$R_1-O_2C(CH_2)_8CO_2-R_2$$

where $R_1$ is selected from the group consisting of ethyl, propyl, n-butyl, 2-ethylhexyl, and combinations thereof, and where $R_2$ is selected from the group consisting of ethyl, propyl, n-butyl, 2-ethylhexyl, and combinations thereof.

In certain embodiments, step 210 includes forming Applicant's coating composition by; adding a dialkylester of decanedioic acid, such a di-n-butyl-sebacate, to a 30 percent solids aqueous dispersion of a polymeric cellulose acetate phthalate polymer with stirring/agitation over a period of about 30 minutes. In step 220, this coating composition is applied to Applicant's first beads.

In step 220, the first beads are encapsulated with Applicant's coating composition of step 210. The amount of coating to be used in forming Applicant's second dosage form will be determined by the desired delivery properties, including the amount of drug to be delivered, the delay time required, and the size of the particles. The appropriate amount of coating can advantageously be determined using in vitro measurements of drug release rates obtained with selected amounts of coating. The coating can be deposited by any method known to those skilled in the art, such as spray application. Spraying can be carried out by pan coating or by use of a fluid bed, such as the Wurster fluidized bed described above.

In step 230 Applicant's second sealing composition is formed. In step 230, a second hydroxypropylalkylcellulose, a second polyether polyol, and talc are combined to form Applicant's second sealant material. In certain embodiments, the second hydroxypropylalkylcellulose used in step 230 is the same as the first hydroxypropylalkylcellulose used in step 140. In certain embodiments, the second hydroxypropylalkylcellulose used in step 230 differs from the first hydroxypropylalkylcellulose used in step 140. In certain embodiments, the second hydroxypropylalkylcellulose comprises hydroxypropylmethylcellulose.

Applicant's second sealing composition comprises Applicant's second sealant material in combination with water. In certain embodiments, Applicant's second sealing material is present in Applicant's second sealing composition at a level between about 25 weight/volume percent and about 55 weight/volume percent. In certain embodiments, Applicant's second sealing material is present in Applicant's second sealing composition at a level between about 30 weight/volume percent and about 50 weight/volume percent. In certain embodiments, Applicant's second sealing material is present in Applicant's sealing composition at a level of about 45 weight/volume percent, i.e. about 45 grams of second sealing material in about 100 ml of water.

In certain embodiments, the talc used in step 230 comprises Magnesium Silicate Hydroxide, i.e. $Mg_3Si_4O_{10}(OH)_2$. In certain embodiments, the talc used in step 230 comprises Magnesium metasilicate, i.e. $MgSiO_3$. In certain embodiments, the talc used in step 230 comprises Magnesium orthosilicate, i.e. $Mg_2SiO_4$.

In certain embodiments the second polyether polyol used in step 230 comprises a polyethyleneoxide diol. In certain embodiments, the second polyether polyol used in step 230 comprises a polyethyleneoxide triol. In certain embodiments, the second polyol used in step 230 comprises a polypropyleneoxide diol. In certain embodiments, the second polyol used in step 230 comprises a polypropyleneoxide triol. In certain embodiments, the second polyol used in step 230 comprises a tetramethyleneoxide diol. In certain embodiments, the second polyol used in step 230 comprises a tetramethyleneoxide triol.

In certain embodiments, the second polyether polyol used in step 230 has a hydroxyl equivalent weight of between about 100 and about 800. In certain embodiments, the second polyether polyol used in step 230 has a hydroxyl equivalent weight of between about 200 and about 600. In certain embodiments, the second polyether polyol used in step 230 has a number average molecular weight of between about 200 and about 800.

In certain embodiments, the first polyether polyol used in step 140 is the same as the second polyether polyol used in step 230. In certain embodiments, the first polyether polyol used in step 140 differs from the second polyether polyol used in step 230.

The embodiments of step 240 are similar to the embodiments of step 145 discussed above.

In step 250, the polymer-coated and sealed first beads are dried to form second beads 400. In certain embodiments, step 250 includes drying the polymer-coated and sealed first beads in the fluidized bed used to apply the second sealing coating of step 240. In certain embodiments, step 250 includes drying the polymer-coated and sealed first beads in the fluidized bed for about five minutes. In certain embodiments, step 250 includes drying the polymer-coated and sealed first beads in an air oven. In certain embodiments, step 250 includes drying the polymer-coated and sealed first beads in an air oven for about 2 hours at about 65° C. In certain embodiments, step 250 includes drying the polymer-coated and sealed first beads in an air oven for about 24 hours at about 55° C.

Figure 4:
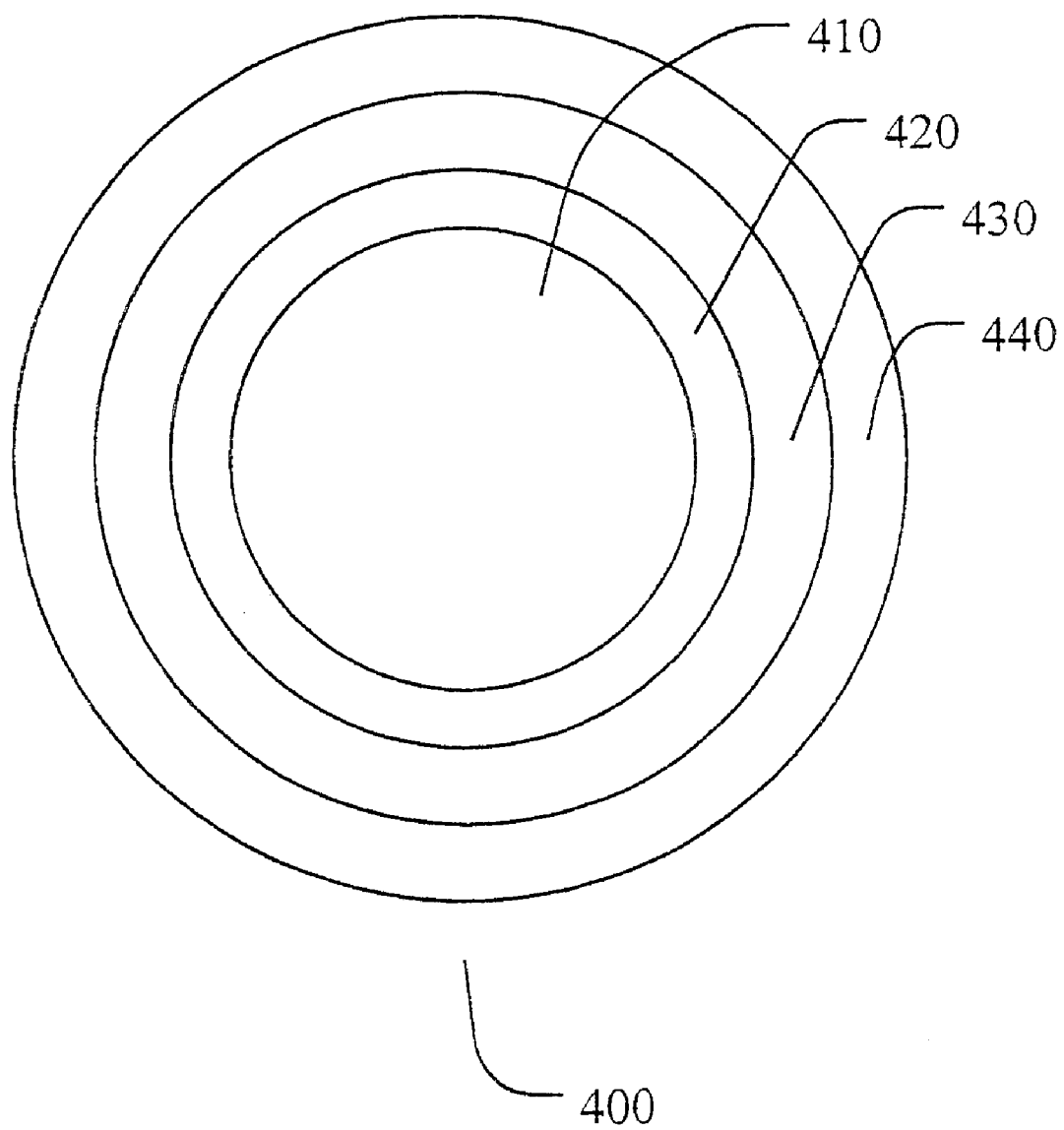
FIG. 4 is a cross sectional view of one embodiment of Applicant's second pulse dosage.

Referring to FIG. 4, Applicant's second bead 400 formed in step 250 (FIG. 2) includes Methylphenidate-containing component 410, first sealing layer 420 disposed over component 410, polymeric coating layer 430 disposed over first sealing layer 420, and second sealing layer 440 disposed over polymeric coating layer 430. Methylphenidate-containing component 410 comprises Applicant's spheres resulting from the separation of step 135 (FIG. 1). First sealing layer 420 is applied in step 145 (FIG. 1). Second sealing layer 430 is applied in step 240 (FIG. 2).

In certain embodiments, Methylphenidate-containing portion 410 is present in Applicant's second beads 400 at a level between about 22 weight percent and about 60 weight percent. In certain embodiments, Methylphenidate-containing portion 410 is present in second bead 400 at a level between about 40 weight percent and about 55 weight percent. In certain embodiments, Methylphenidate-containing portion 410 is present in second bead 400 at a level of about 48 weight percent.

Referring again to FIG. 2, in step 260 the plurality of second beads 400 formed in step 250 are separated by size. In certain embodiments, step 260 includes separating second beads 400 using a 12 mesh screen. In certain embodiments, step 260 includes separating second beads 400 that pass through a 12 mesh screen using a 25 mesh screen. In certain embodiments, the second beads 400 that pass through a 12 mesh screen, but do not pass through a 25 mesh screen, comprise Applicant's second pulse dosage.

As those skilled in the art will appreciate, the quantities of Methylphenidate delivered by Applicant's first pulse dosage and by Applicant's second pulse dosage depends upon the prescribed dosage to be delivered to a patient. According to Applicant's method, Applicant's first pulse dosage and Applicant's second pulse dosage can be administered simultaneously as part of one dosage form. Any dosage form can be used. For example, the two groups of particles can be combined within a capsule. Alternatively, the two groups of particles can be pressed into a solid form such as a tablet. In pressing the particles into a solid form, suitable processing aids known to those skilled in the art can be used. Alternatively, Applicant's second pulse dosage can be dispersed within or blended with, Methylphenidate in powder form. The Methylphenidate delivered to the patient by Applicant's first pulse dosage is preferably released within about 30 minutes, more preferably about 15 minutes, and most preferably within about 5 minutes following ingestion.

Figure 5:
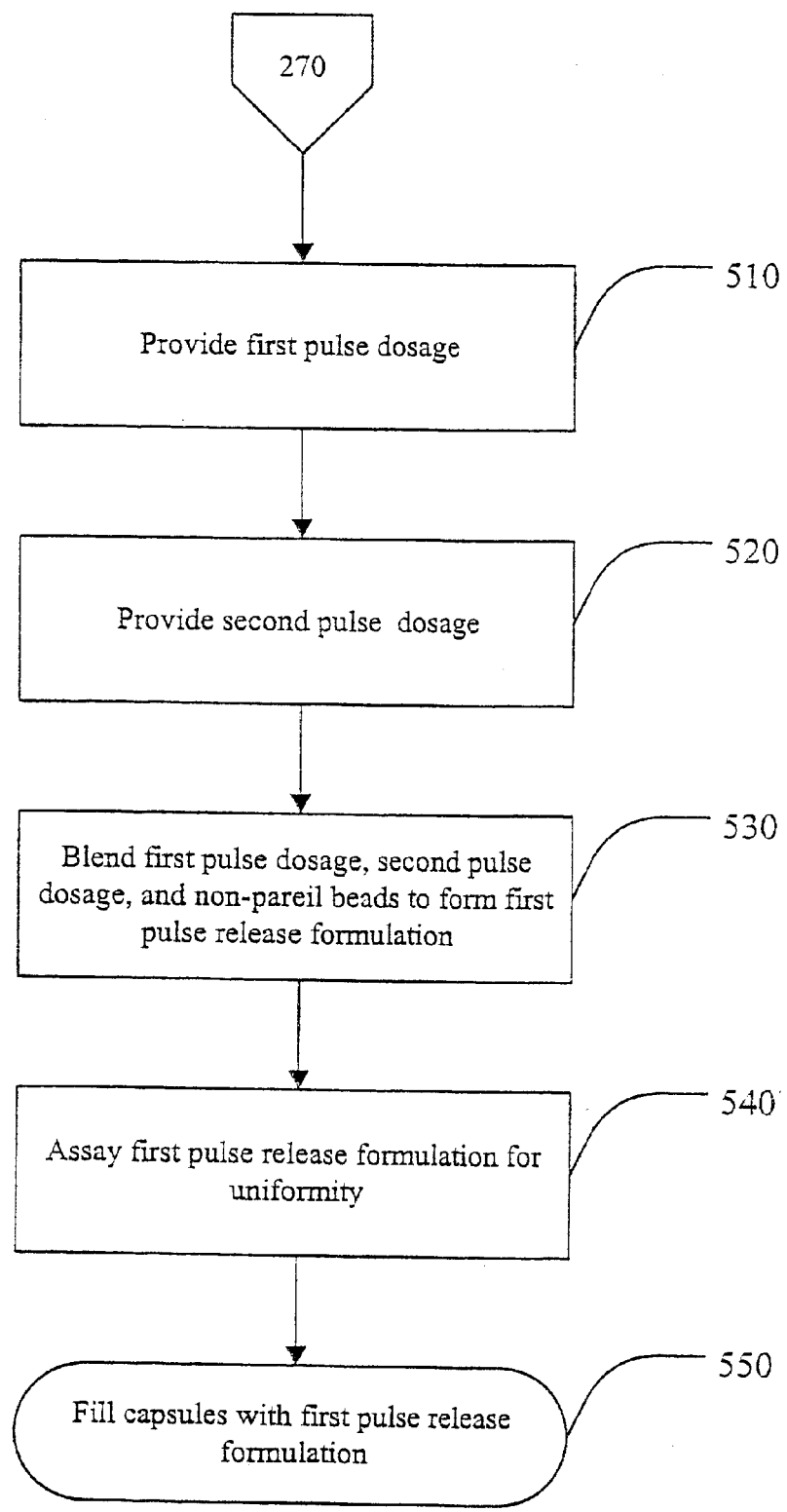
FIG. 5 is a flowchart summarizing the steps of Applicant's method to prepare Applicant's first pulse release formulation.

FIG. 5 summarizes the steps of Applicant's method to prepare Applicant's first pulse formulation which includes Applicant's first pulse dosage in combination with Applicant's second pulse dosage. In certain embodiments, Applicant's first pulse release formulation includes a #4 gelatin capsule filled with about 140 mg of material.

To prepare a first embodiment of Applicant's first pulse release formulation, where that first embodiment provides a dosage of about ten (10) mg of Methylphenidate over a time period of about nine (9) hours, in step 510 a quantity of Applicant's first pulse dosage equivalent to 3 mg of Methylphenidate is provided. That first pulse dosage is prepared in accord with the steps shown in FIG. 1 and described above. In certain embodiments, Applicant's first pulse dosage comprises about 55.5 weight percent Methylphenidate. Using such an embodiment of Applicant's first pulse dosage, about 5.4 mg of that first pulse dosage comprises about 3 mg of Methylphenidate.

In step 520, a quantity of Applicant's second pulse dosage equivalent to 7 mg of Methylphenidate is provided. That second pulse dosage is prepared in accord with the steps shown in FIGS. 1 and 2, as described above. In certain embodiments, Applicant's second pulse dosage comprises about 48.0 weight percent Methylphenidate. Using such an embodiment of Applicant's second pulse dosage to form this first embodiment of Applicant's first pulse release formulation, about 14.5 mg of that second pulse dosage comprises about 7 mg of Methylphenidate.

To prepare this first embodiment of Applicant's first pulse release formulation which delivers about 10 mg of Methylphenidate over about a 9 hour period, in step 530 the quantity of Applicant's first pulse dosage determined in step 410, i.e. about 5.4 mg of the 55.5% Methylphenidate embodiment of Applicant's first pulse dosage, along with the quantity, of Applicant's second pulse dosage determined in step 520, i.e. about 14.5 mg of the 48% Methylphenidate embodiment of Applicant's second pulse dosage, in combination with about, 120 mg of blank non-pareil beads, are combined. In certain embodiments, step 530 includes blending Applicant's first pulse dosage, Applicant's second pulse dosage, and the non-pareil beads using a PK-V type blender. In certain embodiments, step 530 includes use of such a blender for about 10 minutes.

In step 540, the blend of step 530 is assayed for uniformity. In step 550, the blend of step 530 is disposed into a plurality of #4 gelatin capsules, where each of those capsules contains about 140 mg of material.

To prepare, for example, a second embodiment of Applicant's first pulse release formulation which provides a dosage of about twenty (20) mg of Methylphenidate over about a 9 hour period, step 510 comprises providing about 10.8 mg of the 55.5% Methylphenidate-containing embodiment of Applicant's first pulse dosage. Step 520 comprises providing about 29 mg of the 48% Methylphenidate-containing embodiment of Applicant's second pulse dosage.

In step 530, the afore-recited amounts of Applicant's first pulse dosage and second pulse dosage are blended with about 100 mg of blank non-pareil beads. Thereafter, steps 540 and 550 are as described above.

Figure 6:
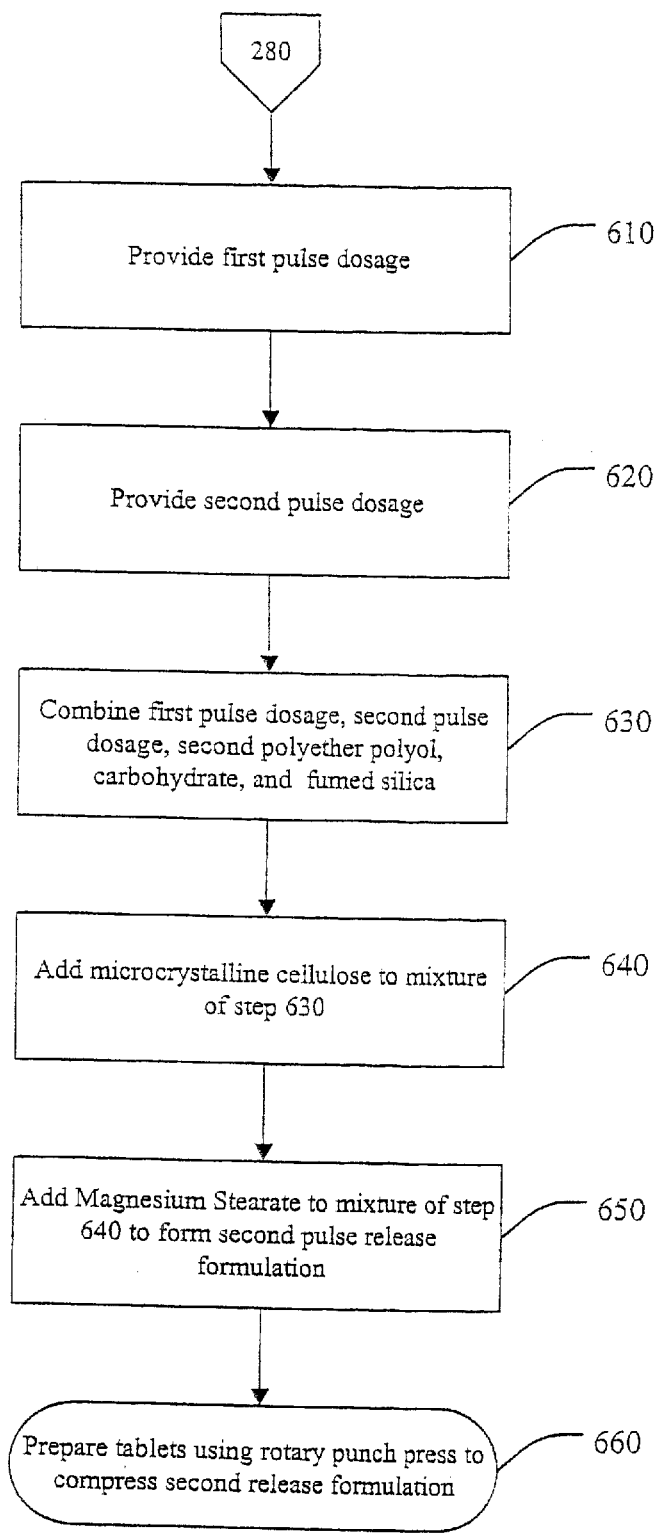
FIG. 6 is a flow chart summarizing the steps of Applicanit's method to prepare Applicant's second pulse release formulation.

FIG. 6 summarizes the steps of Applicant's method to prepare Applicant's second pulse release formulation which includes Applicant's first pulse dosage in combination with Applicant's second pulse dosage. In certain embodiments, Applicant's second pulse release formulation comprises a tablet.

To prepare a first embodiment of Applicant's second pulse release formulation which provides a dosage of about ten (10) mg of Methylphenidate over a time period of about nine (9) hours, in step 610 a quantity of Applicant's first pulse dosage equivalent to 3 mg of Methylphenidate is provided. In certain embodiments, Applicant's first pulse dosage comprises about 55.5 weight percent Methylphenidate. In order to prepare 5,000 tablets using such an embodiment of Applicant's first pulse dosage, about 27 grams of that first pulse dosage are provided in step 610.

In step 620, a quantity of Applicant's second pulse dosage equivalent to 7 mg of Methylphenidate is provided. In certain embodiments, Applicant's second pulse dosage comprises about 48.0 weight percent Methylphenidate. In order to prepare 5,000 tablets using such an embodiment of Applicant's second pulse dosage, about 72.5 grams of that second pulse dosage are provided in step 620.

To prepare 5,000 tablets comprising this first embodiment of Applicant's second pulse release formulation, in step 630 about 27 grams of Applicant's first pulse dosage 300, about 72.5 grams of Applicant's second pulse dosage 350, about 12 grams of a third polyether polyol, about 5 grams of fumed silica, and about 177 grams of a dried carbohydrate, are blended. In certain embodiments, the third polyether polyol comprises a polyethylene oxide glycol. In certain embodiments, the polyether polyol comprises Carbowax Sentry PEG 3350 NF (formerly sold in commerce as PEG 3350 NF).

As those skilled in the art will appreciate, many polyols and carbohydrates are hygroscopic. Applicant has found, however, that the third polyether polyol and the carbohydrate used in step 630 are preferably substantially moisture free. In certain embodiments, the third polyol and the carbohydrate used in step 630 are first dried to moisture levels of about one weight percent or less. In embodiments, the carbohydrate used in step 630 comprises a spray-dried monosaccharide. In certain embodiments, the carbohydrate of step 630 comprises spray-dried lactose. In certain embodiments, step 630 includes using a PK-V blender. In certain embodiments, step 630 includes using such a blender for about 15 minutes.

In step 640, about 400 grams of microcrystalline cellulose particles are added to the mixture of step 630. In certain embodiments, the microcrystalline cellulose particles have a typical particle size of about 50 microns and about 200 microns. In certain embodiments, the microcrystalline cellulose particles have a bulk density of between about 0.25 g/cc and about 0.45 g/cc. In certain embodiments, the microcrystalline cellulose particles have a typical particle size of about 50 microns and a bulk density of about 0.29 g/cc. In certain embodiments, step 640 includes using a PK-V blender. In certain embodiments, step 640 includes using such a blender for about 15 minutes.

In step 650, about 6 grams of Magnesium Stearate are added to the mixture of step 640. In certain embodiments, step 650 includes using a PK-V blender. In certain embodiments, step 650 includes using such a blender for between about 1 minute and about 15 minutes.

In step 660, the mixture of step 650 is compressed using a rotary punch press. In certain embodiments, this punch press includes $9/32$ inch concave punches. In certain embodiments, step 660 includes preparing tablets that weight about 140 mg having a hardness of 3 kilopounds.

To prepare, for example, 5,000 tablets of a second embodiment of Applicant's second pulse release formulation, where each tablet delivers a total dose of about twenty (20) mg of Methylphenidate over about a 9 hour period, then step 630 comprises blending about 54 grams of the 55.5% Methylphenidate-containing embodiment of Applicant's first pulse dosage, about 145 grams of the 48% Methylphenidate-containing embodiment of Applicant's second pulse dosage, about 24 grams of third polyether polyol, about 5 grams of fumed silica, and about 134 grams of carbohydrate. In prepare this embodiment, step 640 includes adding about 330 grams of microcrystalline cellulose to the mixture of step 630. Steps 650 and 660 in this second embodiment are as described above for preparing the first embodiment of Applicant's second pulse release formulation.

The dosage forms provided by the invention can be of any shape suitable for oral administration of a drug, such as spheroidal, cube-shaped, oval, bean shaped, or ellipsoidal. The dosage form may be in the form of granules, which may be irregularly shaped. In any of the embodiments of the present invention, although the size of the particles is generally not critical, a certain particle size or sizes can be preferred depending upon the characteristics of the dosage form. For example, the dosage form can comprise a capsule containing a first and second group of particles. The particles should then be of a size which allows for ease in handling, and which allows for the particles comprising a desired quantity of drug to be readily measured and inserted into the capsule. If the dosage form comprises a single group of particles providing a substantially immediate dose and a delayed dose, the particles are preferably of a size and shape which facilitate oral administration. For example, the particles can be in the form of tablets, caplets, etc. Alternatively, the particles can be contained within a capsule of suitable size and shape for oral administration. If desired, various fillers and/or binders known to those skilled in the art can be included in the particles to provide the desired size and shape.

It will be recognized by one skilled in the art that the dosage forms of the present invention may include, in either or both of the first pulse dosage and the second pulse dosage, pharmaceutically acceptable carriers, extenders, fillers, processing aids, and excipients known to those skilled in the art.

The following examples are merely illustrative of the present invention and should not be considered limiting of the scope of the invention in any way. These examples and equivalents thereof will become more apparent to those skilled in the art in light of the present disclosure and the accompanying claims.

EXAMPLE I

Preparation of First Pulse Dosage

To a planetary mixer were added 40 gram of Methylphenidate, 20 grams of Avicel PH 101, and 10 grams of spray-dried lactose. The materials were blended for about 15 minutes. Over a period of about 5 to about 10 minutes, about 20 to about 250 ml of water was added until a dough-like consistency is obtained. Avicel PH 101 is sold by FMC BioPolymer.

The dough-like mixture was extruded using a basket extruder having $3/64$ inch openings. The cylindrically-shaped, dough-like extrudate were fed into a 10 inch spheronizer operating at about 1,000 r.p.m., and were spheronized for about 10 seconds. The resulting spherically-shaped materials were removed from the spheronizer and were tray-dried in an air oven maintained at about 45° C. until the moisture content was below about 2 weight percent. The dried spheres were separated by size. Those spheres passing through a 12 mesh screen, but not passing through a 25 mesh screen, comprise Applicant's first pulse dosage. The "fines," i.e. those spheres passing through the 25 mesh screen, and the "oversizes," i.e. those spheres not passing through the 12 mesh screen, were recovered and weighed.

Applicant's first sealing composition was prepared by dissolving about 2 grams of HPMC (Methocel E5) in hot water. That solution was then diluted with 15 ml of deionized water. To this solution was added about 2 grams of Carbowax PEG 400 and about 2 grams of talc. Carbowax PEG 400 is sold by Dow Chemical. Talc is sold by the Feldspar Corporation.

Applicant's first sealing composition was applied to the size-separated spheres formed above using a Wurster fluid bed having a bottom spray configuration. The fluidization airflow was about 70–80 $mn^3$/hour. The atomization pressure was 1.5 bar. The spray rate was between about 2 to about 5 grams per minute. The first sealing composition covered spheres were dried in the fluid bed for about 5 minutes at about 50° C. Thereafter, the sealed spheres were dried on trays in an air dryer for about 24 hours at about 55° C. to form first beads.

The first beads were size separated using a 12 mesh and a 25 mesh screen. Those first beads that passed through the 12 mesh screen, but did not pass through the 25 mesh screen, comprise Applicant's first pulse dosage.

EXAMPLE II

Preparation of Second Pulse Dosage

A polymeric coating was prepared by stirring for about 30 minutes about 60 grams of Aquacoat CP and abut 4.5 grams dibutyl sebacate. Aquacoat CPD is sold by FMC BioPolymer. About 50 grams of Applicant's first beads were coated with about 27 grams of the above-described polymeric coating using a Wurster fluidized bed. The fluidization airflow was 70–80 $m^3$. The atomization air pressure was 1.5 bar. The spray rate was 4–10 ml per minute. The fluidized bed was operated at a temperature of about 42° C. The polymeric coating was dried for about 5 minutes in the coating apparatus.

Applicant's second sealing composition was prepared by dissolving about 2 grams of IAPMC (Methocel E5) in hot water. That solution was then diluted with 15 ml of distilled water. To this solution was added about 2 grams of Carbowax PEG 400 and about 2 grams of talc. Carbowax PEG 400 is sold by Dow Chemical. Talc is sold by the Feldspar Corporation.

Applicant's second sealing composition was applied to the polymer-coated first beads using a Wurster fluid bed having a bottom spray configuration. The fluidization airflow was about 70–80 $m^3$/hour. The atomization pressure was 1.5 bar. The spray rate was between about 2 to about 5 grams per minute.

The second sealing composition covered, polymer-coated first beads were dried for about 5 minutes in the fluid bed. Thereafter, the second sealing composition covered, polymer-coated first beads were dried in an air oven for about 2 hours at about 65° C., and then for about 24 hours at about 55° C. to form second beads. Thereafter, the second beads were size separated using a 12 mesh and a 25 mesh screen. Those second beads passing through the 12 mesh screen, but not passing through the 25 mesh screen comprise Applicant's second pulse dosage.

EXAMPLE III

Preparation of First Pulse Release Formulation

About 5.4 mg of an embodiment of Applicant's first pulse dosage comprising about 55.5 weight percent Methylphenidate, about 14.5 mg of an embodiment of Applicant's second pulse dosage comprising about 48.0 weight percent Methylphenidate, and about 120 mg of black non-pareil beads were blended in a PK-V blender for about 10 minutes. The blend was then assayed for uniformity. The blend is then disposed into #4 gelatin capsules, where each capsule contains a total of about 140 mg of the uniform blend.

EXAMPLE IV

Preparation of Second Pulse Release Formulation

To a PK-V blender were added 27 grams of Applicant's first pulse dosage discussed above, where that first pulse dosage comprised about 55.5 weight percent DTMP, 72.5 grams of Applicant's second pulse dosage discussed above, where that second pulse dosage comprised about 48.0 weight percent DTMP, about 12 grams of Carbowax PEG 3350 NF, about 5 grams of Cab-O-Sil M5, and about 177 grams of spray-dried lactose USP. This first mixture was blended for about 15 minutes. Carbowax PEG 3350 NF is sold by Dow Chemical. Cab-O-Sil M5 is sold by the Cabot Corporation.

About 400 grams of Avicel PH-101 were added to the above-described first mixture, and the resulting second mixture blended for about 15 minutes. Avicel PH-101 is sold by FMC BioPolymer.

About 6 grams of magnesium Stearate were added to the above-described second mixture. The resulting third mixture was blended for about 5 minutes.

The third mixture was compressed using a rotary press having $9/32$ inch concave punches to form 5,000 tablets weighing about 140 mg each. Each of these tablets had a hardness of about 3 kilopounds.

While the preferred embodiments of the present invention have been illustrated in detail, it should be apparent that modifications and adaptations to those embodiments may occur to one skilled in the art without departing from the scope of the present invention as set forth in the following claims.

I claim:

1. A dosage form for the oral administration of a methylphenidate drug, comprising a first pulse dosage and a second pulse dosage, wherein:

said first pulse dosage comprises a first methylphenidate drug portion and a first sealing layer, wherein said first sealing layer is disposed over said first methylphenidate drug portion; and said second pulse dosage comprises a second methylphenidate drug portion, a second sealing layer disposed over said second methylphenidate drug portion, a polymeric coating layer disposed over said second sealing layer, and a third sealing layer disposed over said polymeric coating layer.

2. The dosage form of claim 1, wherein said first methylphenidate drug portion comprises a first pharmaceutically acceptable salt of methylphenidate.

3. The dosage form of claim 2, wherein said first pharmaceutically acceptable salt of methylphenidate is d-threo methylphenidate hydrochloride.

4. The dosage form of claim 2, wherein first pharmaceutically acceptable salt of methylphenidate is present at level form between about 22 weight percent to about 65 weight percent.

5. The dosage form of claim 4, wherein said first pharmaceutically acceptable salt of methylphenidate is present at level of about 55 weight percent.

6. The dosage form of claim 1, wherein said second methylphenidate drug portion comprises a second pharmaceutically acceptable salt of methylphenidate.

7. The dosage form of claim 6, wherein said second pharmaceutically acceptable salt of methylphenidate is d-threo methylphenidate hydrochloride.

8. The dosage form of claim 6, wherein said second pharmaceutically acceptable salt of methylphenidate is present at level from between about 20 weight percent to about 60 weight percent.

9. The dosage form of claim 8, wherein said second pharmaceutically acceptable salt of methylphenidate is present at level of about 48 weight percent.

10. The dosage form of claim 1, wherein said first sealing layer comprises:

hydroxypropylalkylcellulose;

a polyether polyol; and talc.

11. The dosage form of claim 10, wherein said polyether polyol comprises a polyethylene oxide glycol.

12. The dosage form of claim 11, wherein said hydroxypropylalkylcellulose comprises hydroxypropylmethylcellulose.

13. The dosage form of claim 1, wherein said polymeric coating layer comprises a cellulose acetate polymer and a dialkyl dicarboxylic acid ester.

14. The dosage form of claim 13, wherein said cellulose acetate polymer comprises a cellulose acetate phthalate polymer.

15. The dosage form of claim 14, wherein said dialkyl dicarboxylic acid ester comprises di-butyl sebacate.

16. A method to form a pulse release formulation comprising a methylphenidate drug, comprising the steps of:

providing said methylphenidate drug;

forming a first mixture comprising said methylphenidate drug, a microcrystalline cellulose, and a polyol;

adding water to said first mixture to form a second mixture, wherein said second mixture has a bulk viscosity greater than about 10,000 cps;

extruding said second mixture to form plurality of cylindrically-shaped particles;

spheronizing said plurality of cylindrically-shaped particles to form a plurality of spheroids;

drying said spheroids to a moisture content of below about 2 weight percent;

separating by size said dried spheroids;

forming a first sealing composition comprising a first hydroxypropylalkylcellulose, a first polyether polyol, and talc;

applying said first sealing composition to said dried spheroids to form first beads;

drying said first beads;

separating said first beads by size to form a first pulse release dosage;

forming a polymeric coating composition comprising a cellulose acetate polymer and a dialkyl ester of dicarboxylic acid;

encapsulating said first beads with said polymeric coating composition;

forming a second sealing composition comprising a second hydroxypropylalkylcellulose and a second polyether polyol;

applying said second sealing composition over said polymeric coating composition;

drying said second sealing composition covered, polymeric composition encapsulated first beads to form second beads;

separating by size said second beads to form second pulse dosage;

providing a plurality of non-pareil beads;

blending said first pulse dosage, said second pulse dosage, and said non-pareil beads to form a pulse release formation; and assaying said pulse release formulation for uniformity.

17. The method of claim 16, further comprising the step of filling a plurality of capsules with said pulse release formulation.

18. A method to form a pulse release formulation comprising a methylphenidate drug, comprising the steps of:

providing said methylphenidate drug;

forming a first mixture comprising said methylphenidate drug, a microcrystalline cellulose, and a polyol;

adding water to said first mixture to form a second mixture, wherein said second mixture has a bulk viscosity greater than about 10,000 cps;

extruding said second mixture to form a plurality of cylindrically-shaped particles;

spheronizing said plurality of cylindrically-shaped particles to form a plurality of spheroids;

drying said spheroids to a moisture content of below about 2 weight percent;

separating by size said dried spheroids;

forming a first sealing composition comprising a first hydroxypropylalkylcellulose, a first polyether polyol, and talc;

applying said first sealing composition to said dried spheroids to form first beads;

drying said first beads;

separating said first beads by size to form a first pulse release dosage;

forming a polymeric coating composition comprising a cellulose acetate polymer and a dialkyl ester of a dicarboxylic acid;

coating said first beads with said polymeric coating composition;

forming a second sealing composition comprising a second hydroxypropylalkylcellulose and a second polyether polyol;

applying said second sealing composition over said polymeric composition encapsulated first beads;

drying said second sealing composition covered, polymeric composition encapsulated first beads to form second beads;

separating by size said second beads to form a second pulse dosage;

combining said first pulse dosage, said second pulse dosage, a third polyether polyol, a carbohydrate, and fumed silica to form, a third mixture;

adding microcrystalline cellulose to said third mixture to form a fourth mixture; and adding magnesium stearate to said fourth mixture to form said pulse release formation.

19. The method of claim 18, further comprising the step of preparing a plurality of tablets using a rotary punch press to compress said pulse release formulation.

20. A method for treating an individual suffering from ADD, comprising administering by to the individual, once daily, the dosage form of claim 1.

21. A method for treating an individual suffering from ADHD, comprising administering to the individual, once daily, the dosage form of claim 1.

22. A method for treating an individual suffering from narcolepsy, comprising administering to the individual, once daily, the dosage form of claim 1.

23. A method for treating an individual suffering from acute depression, comprising administering to the individual, once daily, the dosage form of claim 1.

24. A method for treating an individual suffering from cognitive decline associated with Acquired Immunodeficiency Syndrome ("AIDS") or AIDS-related conditions, comprising administering to the individual, once daily, the dosage form of claim 1.

25. A method for elevating the mood of a terminally ill patient, comprising administering to the patient, once daily, the dosage form of claim 1.

* * * * *